United States Patent [19]

Fuzesi et al.

[11] 4,366,265

[45] Dec. 28, 1982

[54] STARCH-AMINE-BASED POLYETHER POLYOLS AND POLYURETHANE FOAMS PREPARED THEREFROM

[75] Inventors: Stephen Fuzesi, Hamden; John G. Bayusik, Wallingford, both of Conn.

[73] Assignee: Olin Corporation, New Haven, Conn.

[21] Appl. No.: 368,333

[22] Filed: Apr. 14, 1982

Related U.S. Application Data

[62] Division of Ser. No. 218,870, Dec. 22, 1980, Pat. No. 4,342,864.

[51] Int. Cl.³ .................... C08G 18/14; C08G 18/50
[52] U.S. Cl. .................................. 521/167; 536/4.1; 536/50; 536/120; 536/17.2
[58] Field of Search ........................................ 521/167

[56] References Cited

U.S. PATENT DOCUMENTS

| | | | |
|---|---|---|---|
| 3,167,538 | 1/1965 | Kaiser et al. | 260/210 |
| 3,277,213 | 10/1966 | Fuzesi | 260/233.3 |
| 3,296,245 | 1/1967 | Kaiser et al. | 260/210 |
| 3,332,934 | 7/1967 | Booth et al. | 260/209 |
| 3,399,190 | 8/1968 | Fuzesi et al. | 260/233.3 |
| 3,402,170 | 9/1968 | Fuzesi et al. | 260/233.3 |
| 3,541,034 | 11/1970 | Fuzesi et al. | 260/2.5 |
| 3,763,111 | 10/1973 | Fijal | 260/77.5 AQ |

*Primary Examiner*—H. S. Cockeram
*Attorney, Agent, or Firm*—William A. Simons

[57] ABSTRACT

A novel process for the preparation of starch-amine-based polyols which involves reacting starch with a polyhydric alcohol in the presence of an acid catalyst to form a crude polyglucoside reaction product, the proportion of alcohol to starch being at least 0.3 mole of alcohol per glucose unit weight of starch. An amine compound is admixed with the reaction product, and the mixture is then oxyalkylated with a lower alkylene oxide. Polyurethane foams may be prepared by reacting the resulting polyether polyols with an organic polyisocyanate in the presence of a foaming agent and a reaction catalyst. The physical properties of the resulting foams are excellent.

13 Claims, No Drawings

STARCH-AMINE-BASED POLYETHER POLYOLS AND POLYURETHANE FOAMS PREPARED THEREFROM

This is a division, of application Ser. No. 218,870, filed Dec. 22, 1980, now U.S. Pat. No. 4,342,864.

This invention relates to a process for the preparation of starch-amine-based polyether polyols, to the product resulting from the process, and to the use of these polyols in the preparation of polyurethane foams.

Polyurethane foams have been used in the preparation of structural panels, insulation, cushions, pillows, mattresses, and the like. Generally these foams are prepared by reacting an organic polyisocyanate with a polyol in the presence of a foaming agent and a catalyst. Extensive efforts have been made to reduce the cost of preparing these foams. Because of the low cost of starch, efforts have been made to employ starch as a polyol reactant in the preparation of urethane foams. The use of starch directly has been unsatisfactory, however, because of processing difficulties and the poor physical properties of the foam which results. Oxyalkylated starch yields satisfactory foams, but the direct oxyalkylation of starch results in degradation or decomposition of the starch and a product which is not uniform in chemical or physical properties.

A satisfactory process for utilizing starch as a component in the preparation of polyurethane foams is disclosed in U.S. Pat. No. 3,277,213 issued to Stephen Fuzesi on Oct. 4, 1966. In this process starch is added to a polyhydric alcohol containing at least two hydroxyl groups in a proportion equivalent to at least 0.3 mole of the alcohol per mole of glucose unit weight of starch in the presence of an acid catalyst. The resulting mixture is then oxyalkylated to yield a polyether polyol suitable for use in preparing polyurethane foams. However, there is no disclosure in this patent of adding an amine compound as a co-initiator to the mixture prior to oxyalkylation.

It is, therefore, a primary object of the present invention to provide a novel process for preparing a starch-amine-based polyether polyol.

It is a further object of the present invention to provide a novel starch-amine-based product.

It is yet another object of the present invention to provide rigid polyurethane foams having highly satisfactory physical properties by utilizing the novel starch-amine-based polyether polyols.

These and other objects of the invention will be apparent from the following detailed description thereof.

It has now been discovered that the objects of the invention may be accomplished by: reacting starch and a polyhydric alcohol in the presence of an acid catalyst to form a crude polyglucoside reaction product, the proportion of alcohol to starch being at least 0.3 mole of alcohol per glucose unit weight of starch; and admixing this crude product with an amine, and oxyalkylating the mixture with an alkylene oxide having from 2 to about 6 carbon atoms. The resulting polyether polyols may then be reacted with an organic polyisocyanate, a foaming agent and a catalyst to yield urethane foams having excellent physical properties.

The starch-amine-based polyether polyol of this invention may be prepared from any starch, i.e., any compound having the formula $(C_6H_{10}O_5)_x$. These compounds are carbohydrates or polysaccharides which occur naturally in many plant cells. Typical starches which may be conveniently employed include potato starch, corn starch, chlorinated starches, rice starch, tapioca starch, wheat starch, mixtures thereof and the like. From an economic standpoint, potato starch and corn starch are preferred.

Any polyhydric alcohol containing at least two hydroxyl groups may be employed in the preparation of the starch-amine-based polyol of this invention. It is preferred, however, to employ glycerol, ethylene glycol, diethylene glycol, propylene glycol, dipropylene glycol, sorbitol and the like due to availability and ease of reaction. However, polyhydric alcohols which may be conveniently employed include, but are not limited to, pentaerythritol, hexanetriol, trimethylol propane, trimethylol ethane, 1,2-butanediol, triethylene glycol, 2-butene-1,4-diol, 2-butyne-1,4-diol, 3-chloro-1,2-propanediol, 2-chloro-1,3-propanediol, mixtures thereof and the like.

The polyhydric alcohol is normally employed in an amount of at least 0.3 mole of polyol per one glucose unit weight of starch. The upper limit of polyhydric alcohol is not critical; however, it is preferred to use from 0.5 to 5 moles of alcohol per one glucose unit weight of starch in order to retain as much as possible of the starch characteristic in the product.

Each glucose unit weight of starch is equivalent to 162 grams of starch on an anhydrous basis. Normally, each glucose unit weight of starch contains water associated therewith. In a preferred embodiment of the present invention, a small amount of water, preferably not more than about 2 moles or 36 grams, per glucose unit weight of starch, is added with the starch. However, smaller or larger proportions of water may be present if desired.

The acid catalyst may be any inorganic or Lewis acid catalyst. Representative Lewis acid catalysts include, but are not limited to, boron trifluoride etherate, aluminum trichloride, ferric chloride, stannic chloride, titanium tetrachloride, etc., and mixtures thereof. Other suitable acid catalysts include inorganic acids such as sulfuric acid, phosphoric acid, hydrochloric acid, hydrofluoric acid, nitric acid and the like. The preferred catalysts are boron trifluoride etherate and sulfuric acid. The acid catalyst is employed in a catalytic proportion to catalyze the reaction between the starch and the polyhydric alcohol. The proportion of catalyst is generally in the range between about 0.5 and about 5, and preferably between about 1 and about 3, percent of the combined weight of the starch and polyhydric alcohol, but greater or lesser proportions may be utilized if desired.

The initial reaction between the starch and the polyhydric alcohol is accelerated by employing elevated temperatures, i.e., preferably in the range between about 60° and about 200° C. The specific temperature of the reaction will vary depending on the degree of completion, reactants employed, time of reaction, and other reaction conditions. Similarly, the reaction time will vary depending upon the temperature of the reaction, reactants employed and the amounts thereof.

In a preferred procedure for carrying out the initial step of the process of the present invention, the starch is slowly added to a hot fluid mixture of the polyhydric alcohol and the acid catalyst which is maintained at a temperature in the range of between about 100° and about 200° C. After the starch has been added, the mixture is maintained at this elevated temperature until the starch is completely dissolved in the reaction mixture.

Generally, at least about 30 minutes, and no more than about 3 hours, are required.

While it is not desired to be bound by theory, it is believed that the starch will degrade in the presence of the polyhydric alcohol and the catalyst forming glucosides. The relative proportions of glucoside compounds in the reaction product will vary depending upon the reactant proportions and the conditions employed in carrying out the reaction.

In the next step of the process of this invention, the crude polyglucoside reaction product is admixed with an amine compound, the amine compound being employed in an amount of at least about 0.1 mole to about 10 moles per glucose unit weight of starch. An oxalkylation catalyst is added; and then, while maintaining the temperature within the range of from about 60° to about 200° C., an alkylene oxide or a mixture of alkylene oxides is introduced, using random or step-wise addition, into the mixture. The resultant oxyalkylated product is a co-oxyalkylated product in that the alkylene oxide reacts with the glucoside components of the crude reaction mixture and with the amine compound.

Oxyalkylation may be conducted with or without separating any water present. When the water is not removed, the water will be oxyalkylated and will produce an oxyalkylated diol as a constituent of the starch-amine-based polyether polyol.

In the process of the present invention, any suitable amine compound, including mixtures of compounds containing an amine, may be employed. Suitable amines include the following and mixtures thereof:

a. The primary aliphatic amines including mono-, di-, and triamines. These amines usually contain 1-8, and preferably 1-4, carbon atoms such as methylamine, ethylamine, n-propylamine, n-butylamine, n-amylamine, n-hexylamine, ethylene diamine, diaminopropane, diaminobutane, pentamethylene diamine, diethylene triamine, and mixtures thereof. Particularly preferred amines in this group are the diamines having 2-4 carbon atoms such as ethylene diamine.

b. The primary aromatic amines including mono-, di-, and triamines. Preferably these contain 6-8 carbon atoms such as aniline, methylaniline, phenylene diamine, toluene diamine and triaminobenzene. A particularly preferred amine in this group is toluene diamine which may be any isomer, such as 2,3-, 2,4-, and 2,6-toluene diamine, or a mixture of such isomers.

c. The alkanolamines, i.e., the aliphatic hydroxy amines. Usually each alkanol group in these amines contains from 2 to 5 carbon atoms. Illustrative are ethanolamine, diethanolamine, triethanolamine, the mono-, di-, and tripropanolamines, ethanolpropanolamine, diethanolpropanolamine, and the mono-, di-, and tributanolamines. Particularly preferred alkanolamines are those in which each alkanol group contains 2-3 carbon atoms such as the ethanolamines, the propanolamines and the ethanolpropanolamines.

The most preferred amines referred to above are selected from the group consisting of ethylene diamine, diaminopropane, toluene diamine, an ethanolamine such as mono-, di-, and triethanolamine, a propanolamine such as mono-, di-, and tripropanolamine, an ethanolpropanolamine such as monoethanolmonopropanolamine and diethanolpropanolamine, and mixtures of these amines.

Any suitable alkylene oxide, or a mixture of alkylene oxides, may be employed in the process of the present invention. However, it is preferable to utilize a lower alkylene oxide having between 2 and about 6 carbon atoms, such as ethylene oxide or propylene oxide or a mixture thereof.

A variety of conventional oxyalkylating catalysts may be used in carrying out the oxyalkylation reaction. However, it is preferred to employ an alkaline catalyst such as potassium hydroxide. The oxyalkylation reaction is allowed to proceed, usually using elevated temperatures, until a polyol product is obtained which has a hydroxyl number of about 30 to about 800, and preferably about 250 to about 600. The use of elevated temperatures and basic catalysts is conventional in the oxyalkylation art. Proper use of these should be apparent to those skilled in the art. The catalyst is generally employed in an amount of about 1 to about 5 percent by weight of the polyol. The oxyalkylation reaction is initially exothermic and cooling means are employed in order to maintain the reaction at the desired temperature.

In general, after completion of the oxyalkylation reaction, the basic catalyst is neutralized with a mineral acid, such as phosphoric acid, sulfuric acid or hydrochloric acid. The resultant polyol product is then recovered.

Either the so-called "one-shot method" or the "semiprepolymer technique" ("quasiprepolymer technique") may be employed in preparing polyurethane foams from the starch-amine-based polyols.

Any organic polyisocyanate may be employed in the preparation of the polyurethane foams, including diisocyanates, triisocyanates, and polyisocyanates. Organic diisocyanates are preferred due to commercial availablity, especially mixtures of isomers of toluene diisocyanate which are readily available commercially, such as the 4:1 mixture of the 2,4- and 2,6-isomers. Typical exemplificative isocyanates include, but are not limited to, the following: methylene-bis-(4-phenyl isocyanate), 3,3'-bitolylene-4,4'-diisocyanate, 3,3'-dimethoxy-4,4'-biphenylene diisocyanate, naphthalene-1,4-diisocyanate, hexamethylene, diisocyanate, 1,4-phenylene diisocyanate, polymethylene polyisocyanate (such as may be purchased commercially under the trademark "PAPI"), etc., and mixtures thereof. The amount of isocyanate employed in the preparation of the polyurethane foams should be sufficient to provide at least about 0.7 NCO groups based on the number of hydroxyl groups present in the starch-amine-based polyether polyol of the present invention, the number of hydroxyl groups in any additive employed and the number of hydroxyl groups employed in the blowing agent. An excess of isocyanate compound may be conveniently employed; and it is preferable, therefore, to employ about 1.0–1.25 NCO groups based on the number of hydroxyl groups.

The polyurethane foams are prepared in the presence of a foaming agent and a reaction catalyst. The foaming agent employed may be any of those known to be useful for this purpose, such as water, the halogenated hydrocarbons and mixtures thereof. Typical halogenated hydrocarbons include, but are not limited to, the following: monofluorotrichloromethane, difluorodichloromethane, 1,1,2-trichloro-1,2,2-trifluoroethane, methylene chloride, chloroform, carbon tetrachloride, and mixtures thereof. The amount of blowing agent employed may be varied within a wide range. Generally, however, the halogenated hydrocarbons are employed in an amount from 1 to 50 parts by weight per 100 parts by weight of the starch-amine-based polyether polyol of the present invention, and generally the water is employed in an amount of from 0.1 to 10 parts by weight per 100 parts by weight of the starch-amine-based polyether polyol of the present invention.

The polyurethane foams are prepared in the presence of a catalytic amount of a reaction catalyst. The catalyst employed may be any of the catalysts known to be useful for this purpose, including tertiary amines and metallic salts. Typical tertiary amines include, but are not limited to, the following: N-methyl morpholine, N-hydroxyethyl morpholine, dimethylcyclohexylamine, triethylene diamine, triethylamine, trimethylamine and mixtures thereof. Typical metallic salts include, for example, the salts of antimony, tin and iron, e.g., dibutyltin dilaurate, stannous octoate, etc., and mixtures thereof. Generally speaking, the catalyst is employed in an amount from 0.1 to 5 percent by weight based on th starch-amine-based polyether polyol of the present invention.

The polyurethane foams of the present invention may be prepared directly from the reaction between the starch-amine-based polyether polyol and organic polyisocyanate in the presence of a foaming agent and a reaction catalyst. Optionally, various additives may be employed in the preparation of the polyurethane foams in order to achieve particular properties. Exemplificative of such additives include, but are not limited to, the following: halogen and phosphorus-containing reactive and non-reactive type additives to improve flame retardancy, monocarboxylic and polycarboxylic acid-based polyesters, monohydroxy compounds, polyhydroxy compounds, etc.

Some of the starch-amine-based polyols employed in the present invention are characterized by a high room temperature viscosity. In these cases in order to prepare the polyurethane foam it will be necessary to apply heat in order to reduce the viscosity or to admix therewith a material, such as a polyether polyol, of lower viscosity. This may be conveniently accomplished by admixing a lower viscosity starch-amine-based polyol with the higher viscosity starch-amine-based polyol.

It is preferred in the preparation of the polyurethane compounds of the present invention to employ minor amounts of a surfactant in order to improve the cell structure of the polyurethane foam. Typical of such surfactants are the silicone oils and soaps. Generally up to 2 parts by weight of the surfactant is employed per 100 parts of starch-amine-based polyether polyol.

Various additives can be employed which serve to provide different properties, e.g., fillers, such as clay, calcium sulfate, or ammonium phosphate may be added to lower cost and improve physical properties. Ingredients such as dyes may be added for color, and fibrous glass, asbestos, or synthetic fibers may be added for strength. In addition, plasticizers, deodorants and antioxidants may be added.

The process of the invention provides a relatively simple and practically attractive route to preparing starch-amine-based polyether polyols. Furthermore, these polyols can be used in making rigid polyurethane foams having highly satisfactory physical properties. These objectives are achieved at minimum cost and without, at the same time, undermining the physical properties of the resulting polyols or of the polyurethane foams prepared therefrom.

The process of the present invention will be more readily apparent from a consideration of the following illustrative examples. In the following examples the starch employed contained associated therewith about 10 to 15 percent by weight of water. All parts and percentages are by weight unless indicated otherwise.

EXAMPLES 1 AND 2

The hereinbelow outlined general procedure was followed in the preparation of starch-amine-based polyols. The specific formulations are set forth in Table I below.

A 2-gallon, stainless steel reactor was charged with the diethylene glycol and the sulfuric acid. The mixture was heated to 115°-125° C. and the starch was added to the mixture at a rate such as to maintain the temperature between 110°-125° C. The temperature was maintained at 125°-130° C. until the starch was completely dissolved in the reaction mixture. The mixture at that stage is dark in color and bright in appearance.

Approximately 1.0-1.5 hours were required for hydrolysis of the starch. 0.06 Mole of potassium hydroxide was charged into the reaction mixture. The diethanolamine was then added to the mixture and during the addition the temperature was decreased to 100°-110° C. Keeping the temperature at 100°-105° C., excess water was separated so that the water concentration was a maximum of 1.0 percent by weight of the mixture. The temperature was raised to 110°-112° C. and maintained in the range while the alkylene oxide was added. After addition of the alkylene oxide, heating was continued for 30 minutes maintaining the temperature at 110°-112° C. before filtration of the product.

Analysis of the product gave the properties indicated in Table II.

EXAMPLE 3

The hereinbelow outlined general procedure was followed in the preparation of a starch-amine-based polyol. The specific formulation is set forth in Table I below.

A 2-gallon, stainless steel reactor was charged with the diethylene glycol and the sulfuric acid. The mixture was heated to 115°-125° C. and the starch was added to the mixture at a rate such as to maintain the temperature between 110°-125° C. The temperature was maintained at 125°-130° C. until the starch was completely dissolved in the reaction mixture. The mixture at that stage is dark in color and bright in appearance.

Approximately 1.0-1.5 hours were required for hydrolysis of the starch. 0.06 Mole of potassium hydroxide was charged into the reaction mixture. The diethanolamine was then added to the mixture and during the addition the temperature was decreased to 110°-112° C. Water was condensed. Keeping the temperature at 110°-112° C., and without separating the water, alkylene oxide was added. After addition of the alkylene oxide, heating was continued for 30 minutes maintaining the temperature at 110°-112° before filtration of the product.

Analysis of the product gave the properties indicated in Table II.

TABLE I

| Component | Example | | |
|---|---|---|---|
| (Moles) | 1 | 2 | 3 |
| Starch.H$_2$O | 2.0 | 2.0 | 2.0 |
| Diethylene Glycol | 1.0 | 1.0 | 1.0 |
| Sulfuric Acid | 0.025 | 0.025 | 0.025 |
| Diethanolamine | 2.25 | 3.56 | 2.25 |
| Propylene Oxide | 15.4 | 14.87 | 22.10 |

TABLE I-continued

| Component | Example | | |
|---|---|---|---|
| (Moles) | 1 | 2 | 3 |
| Ethylene Oxide | — | 7.02 | — |

TABLE II

| Property | Example | | |
|---|---|---|---|
| | 1 | 2 | 3 |
| Hydroxyl Number | 530 | 502 | 529 |
| Nitrogen, percent | 1.86 | 2.40 | 1.58 |

EXAMPLE 4

A rigid polyurethane foam was prepared from the product of Example 1 by admixing the following ingredients in the following proportions:

| Ingredient | Amount (Grams) |
|---|---|
| Liquid Product of Example 1 | 100 |
| Dow Corning ® 191 surfactant[1] | 2 |
| Dimethylcyclohexylamine catalyst[2] | 4 |
| Trichloromonofluoromethane blowing agent[3] | 37.4 |
| Polymethylene polyphenylisocyanate[4] | 145 |

[1]This is a silicone-glycol copolymer described in 1977 Dow Corning bulletin, No. 22-476-77.
[2]This is a commercial product of Abbott Laboratories purchased under the trademark "Polycat-8".
[3]This is a commercial product of E. I. DuPont de Nemours and Company purchased under the trademark "R-11 B".
[4]This is a commercial product of Upjohn Company purchased under the trademark "PAPI-135" and having an approximate functionality of 2.6.

The mixture was allowed to foam and was cured at elevated temperatures. The resultant rigid polyurethane foam had the physical properties listed in Table III.

EXAMPLES 5 AND 6

In the following Examples, the procedure of Example 4 was repeated except that the products of Examples 2 and 3 were used in Examples 5 and 6, respectively. The resultant rigid polyurethane foam had the physical properties listed in Table III.

TABLE III

| | Example | | |
|---|---|---|---|
| | 4 | 5 | 6 |
| Liquid Product, Example | 1 | 2 | 3 |
| Cream, sec. | 16 | 8 | 12 |
| Gel, sec. | 49 | 24 | 48 |
| T. Free, sec. | 76 | 38 | 68 |
| Rise, sec. | 103 | 56 | 92 |
| Density, p.c.f. | 1.95 | 1.84 | 2.03 |
| Compressive Strength, p.s.i. | 41.80 | 42.10 | 30.65 |
| Compressive Strength, p.s.i. | 20.90 | 17.00 | 17.90 |
| C-Factor | 0.118 | 0.119 | — |
| K-Factor | — | — | 0.142 |
| Friability | 8.22 | 3.07 | 3.27 |
| Porosity | 85.09 | 85.12 | 78.74 |
| Dry Heat Age, @ 200° F. | 4.22 | 6.20 | 5.13 |
| Dry Heat Age, @ 230° F. | 13.99 | 12.52 | 13.50 |
| Humid Age, @ 158° F./100% RH | 11.59 | 13.46 | 10.34 |

What is claimed is:

1. In a polyurethane foam comprised of the reaction product of a polyol reactant, an organic polyisocyanate reactant, a reaction catalyst and a foaming agent, the improvement wherein said polyol reactant is prepared by:
    a. forming a crude polyglucoside reaction product by reacting in the presence of a catalytic proportion of an acid catalyst,
        (1) starch and
        (2) a polyhydric alcohol containing at least two hydroxyl groups, the proportion of said alcohol being at least 0.3 mole of alcohol per glucose unit weight of starch, and
    b. admixing said crude polyglucoside reaction product with an amine in the presence of a basic catalyst, maintaining said mixture at a temperature of from 100° to 165° C., and introducing into said mixture an alkylene oxide having between 2 and about 6 carbon atoms, said amine being employed in an amount of at least about 0.1 mole to about 10 moles per glucose unit weight of starch and being selected from the group consisting of an aliphatic amine having 1–8 carbon atoms, an aromatic primary amine having 6–8 carbon atoms, an alkanolamine in which each alkanol group contains 2–5 carbon atoms, and a mixture thereof.

2. The polyurethane foam of claim 1, wherein said starch is corn starch.

3. The polyurethane foam of claim 1, wherein said acid catalyst is sulfuric acid.

4. The polyurethane foam of claim 1, wherein said alkylene oxide is propylene oxide.

5. The polyurethane foam of claim 1, wherein said alkylene oxide is a mixture of propylene oxide and ethylene oxide.

6. The polyurethane foam of claim 1, wherein said aliphatic amine is a diamine having 2–4 carbon atoms, said aromatic amine is toluene diamine, and said alkanolamine is an ethanolamine, a propanolamine or an ethanolpropanolamine.

7. The polyurethane foam of claim 1, wherein said amine is selected from the group consisting of ethylene diamine, toluene diamine, an ethanolamine, and a mixture thereof.

8. The polyurethane foam of claim 1, wherein water is separated from said crude polyglucoside reaction product prior to reaction with said alkylene oxide.

9. The polyurethane foam of claim 1, wherein said amine is an ethanolamine.

10. The process of claim 9, wherein said starch is corn starch.

11. The process of claim 10, wherein said acid catalyst is sulfuric acid.

12. The process of claim 11, wherein said alkylene oxide is propylene oxide.

13. The process of claim 11, wherein said alkylene oxide is a mixture of propylene oxide and ethylene oxide.

* * * * *